United States Patent [19]
Guillot et al.

[11] Patent Number: 5,229,973
[45] Date of Patent: Jul. 20, 1993

[54] METHOD OF SELECTING ULTRASONIC TRANSDUCERS FOR USE IN ULTRASONIC INSPECTION APPARATUS

[75] Inventors: Eric Guillot, Vincennes; Pierre M. Jagnoux, Draveil; Gérard Y. Mangenet, Brunoy, all of France

[73] Assignee: Societe Nationale D'Etude et de Construction de Moteurs D'Aviation "S.N.E.C.M.A.", Paris, France

[21] Appl. No.: 866,424

[22] Filed: Apr. 10, 1992

[30] Foreign Application Priority Data

Apr. 10, 1991 [FR] France ................ 91 04327

[51] Int. Cl.$^5$ .............................. H04B 17/00
[52] U.S. Cl. ...................... 367/13; 367/191; 181/0.5; 73/1 DV
[58] Field of Search ............. 367/191, 13; 181/0.5; 73/1 R, 1 DV

[56] References Cited

U.S. PATENT DOCUMENTS 3,659,255 4/1972 Trott ................................ 367/191
4,434,648 3/1984 Drost et al. ..................... 73/1 DV

OTHER PUBLICATIONS

"Tone-Burst Testing of Pulse-Echo Transducers", by K. Erikson, *IEEE Transactions on Sonics and Ultrasonics*, vol. Su-26, No. 1 Jan. 1979.
"Acoustic Emission Transducer Calibrator" by W. Leschek, *Materials Evaluation*, vol. 33, No. 2, Feb. 1975.
"Vibration Transducer Calibration Using Comparator Method" by K. Unholtz, *Instrument Society of America*, 22 ISA Conference, Sep. 11-14, 1967.
IEEE 1988 Ultrasonics Symposium, vol. 1, Oct. 5, 1988, Chicago, Ill., USA, pp. 895-900, H. A. Kunkel, "New Technique for Characterizing Ultrasonic Transducers Independently of Pulser and Receiver . . .".
Measurement Techniques, vol. 25, No. 3, Apr. 1982, New York, USA, pp. 270-272, I. A. Krivosheef, et al., "Calibration of Piezoelectric Transducers".
Journal of Acoustic Society of America, vol. 78, No. 5, Nov. 1985, New York, USA, pp. 1519-1523, J. D. Aindow, et al., "Quantitative Investigation of Disc Ultrasonic Sources".
La Pratique Du Controle Industriel Par Ultrasons, vol. 2, pp. 53-61, J. L. Pelletier, "Chapitre II-Technologie Du Controle Par Ultra-Sons".

*Primary Examiner*—J. Woodrow Eldred
*Attorney, Agent, or Firm*—Oblon, Spivak, McClelland, Maier & Neustadt

[57] ABSTRACT

A method of selecting the ultrasonic transducers which are used in non destructive ultrasonic inspection apparatus consists of establishing under predetermined conditions the frequency spectra of the transducers under consideration, comparing these spectra with the frequency spectrum of a reference transducer obtained under the same predetermined conditions, and selecting only those transducers of which the frequency spectrum is substantially identical in form to that of the reference transducer.

5 Claims, 1 Drawing Sheet

METHOD OF SELECTING ULTRASONIC TRANSDUCERS FOR USE IN ULTRASONIC INSPECTION APPARATUS

FIELD OF THE INVENTION

The present invention relates to a method of selecting the ultrasonic transducers which are used in non-destructive ultrasonic inspection apparatus.

BACKGROUND OF THE INVENTION

It is known to use ultrasonic inspection apparatus for non-destructive testing or checking of materials and in medical echography. In the field of materials testing, these techniques enable the detection of heterogeneity and defects in the parts under test, as well as the characterization of the defects.

The transducers employed in these ultrasonic inspection devices are designed to generate sound waves from electrical energy which is supplied to them, and the sound waves are propagated in the medium to be tested for reflection by reflectors. The waves thus reflected are received either by the transmitting transducer acting also as a receiver, or by another transducer acting only as a receiver, and are converted by the receiving transducer into electrical signals which are then analyzed.

The life of these transducers is limited, and replacing them with transducers having identical theoretical characteristics should not put the results of the measurements in doubt. However, it has been found that substantial variations can be obtained between the results of tests carried out in an identical manner with different transducers having identical theroetical characteristics, even after calibration. These variations relate in particular to the amplitude of the fault echos, which could vary by up to a factor of 2.

J. L. Pelletier's work: "La Pratique du Controle Industriel par Ultrasons", Volume 2, published by Editions Communications Actives, points out on page 55 that numerous difficulties and errors originate from the transducers and that it is therefore necessary to know their characteristics. The book describes several characteristics to be determined, particularly the operating frequency. The measurement of this frequency is taken by spectral analysis of the echo obtained from a water-/air interface of dimensions which can be regarded as infinite, the beam of the ultrasonic waves emitted being perpendicular to the interface, and the interface being situated at the limit of the near field for plane transducers, or at the focal point for focussed transducers.

In spite of the determination of these characteristics, however, the problem of reliability and reproducibility of ultrasonic inspections has not been solved. The aim of the present invention is to solve this problem by providing a method of selecting transducers for use in ultrasonic inspection apparatus such that substantial uniformity of performance can be assured.

SUMMARY OF THE INVENTION

To this end, according to the invention, there is provided a method of selecting ultrasonic transducers for use in an ultrasonic inspection apparatus, comprising the steps of: determining the frequency spectrum of the echo obtained from a specific reflector using a reference transducer; determining the frequency spectrum of the echo obtained from said reflector using a test transducer under the same conditions as said reference transducer; comparing the form of the frequency spectrum obtained using said test transducer with the form of the frequency spectrum obtained using said reference transducer; and selecting said test transducer for use in said ultrasonic inspection apparatus only if the forms of the compared frequency spectra are substantially identical.

Preferably, the reflector is positioned at the level of the focal point for focussed transducers, or at the level of the limit of the near field for plane transducers.

The specific reflector may be a plane which can be regarded as infinite, having dimensions which are greater than those of the ultrasonic beams emitted by the transducers.

Preferably, the reflector plane is perpendicular to the direction of propagation of the ultrasonic waves emitted by the transducers.

In carrying out the invention, only the form of the compared spectra need be taken into account, since the spectral density of the test transducer can be corrected by calibration on plane or on artificial faults.

The invention will now be described in more detail with reference to a preferred embodiment, given by way of example, and with reference to the attached drawings.

DETAILED DESCRIPTION OF THE INVENTION AND PREFERRED EMBODIMENT

Figure 1:
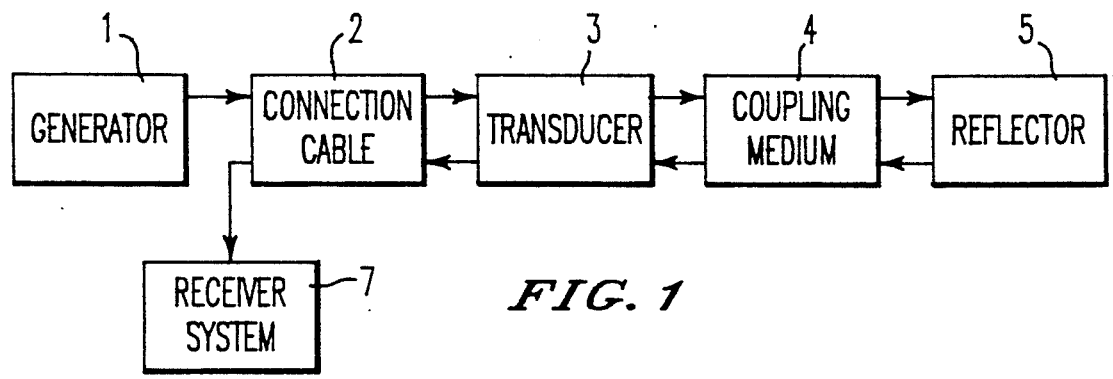
FIG. 1 is a block diagram of an ultrasonic measurement chain.

FIG. 1 shows a standard measurement chain for ultrasonic checking or testing, the chain comprising an electrical pulse generator 1, a cable 2 connecting the generator 1 to a transducer 3 operating as both transmitter and receiver, a coupling medium 4, a reflector 5 for reflecting ultrasonic waves, and a receiver system 7 connected to the transducer 3 by means of the cable 2. Such a measuring chain may be used in carrying out the invention, the receiver system 7 processing the acquired data and possibly displaying the results of the tests, including, for example, the frequency spectra.

Figure 2:
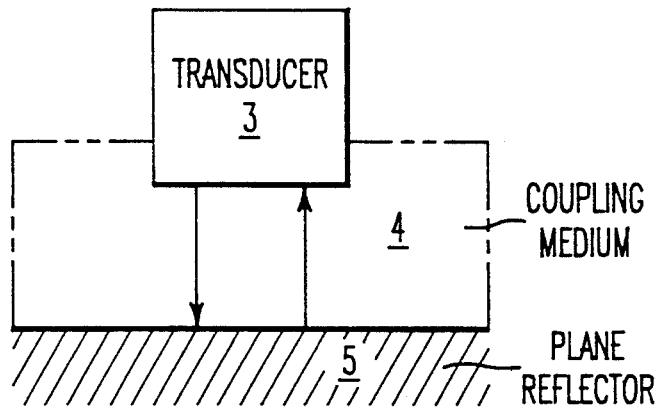
FIG. 2 shows diagrammatically an experimental assembly used in a preferred embodiment of the invention.

FIG. 2 illustrates an experimental assembly used in a preferred embodiment of the invention. This assembly employs the immersion testing technique, wherein a coupling liquid 4 is interposed between the transducer 3 and the reflector 5. The ultrasonic waves emitted by the transducer 3 are reflected by the reflector 5, the beam of the emitted waves being perpendicular to the reflector. This reflector is a plane which is considered infinite, that is to say a plane having dimensions which are greater than those of the beam of ultrasonic waves. The said reflector plane 5 is positioned at the level of the focal point of the focussed transducer 3, i.e. at the position giving the maximum amplitude echo.

Figure 3:
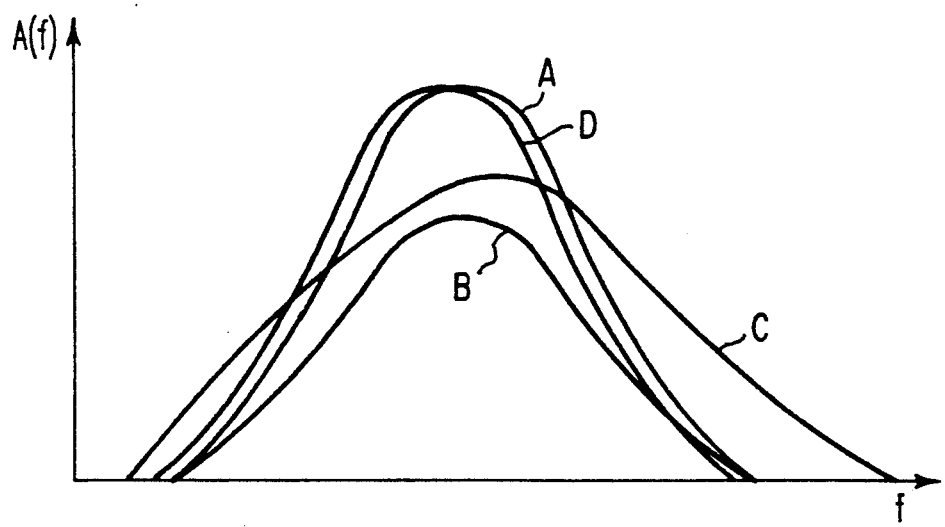
FIG. 3 is a graph showing the frequency spectra of a number of tested transducers and a reference transducer.

FIG. 3 shows examples of the frequency spectra obtained with several different transducers used in an ultrasonic testing apparatus such as described hereinabove with reference to FIGS. 1 and 2.

The method in accordance with the invention involves comparing the forms of these various spectra.

The Applicant has been able to show that if the spectra corresponding to different transducers are identical as to their form and amplitude, the results of measurements taken from signals originating from discontinuities of the material checked with these different transducers are reproducible. If the spectra are identical in form but not in amplitude, it is possible to correct the amplitude differences by calibration on plane or artificial faults by adjusting the amplification or attenuation of the apparatus, thus enabling one to obtain identical spectra and, consequently, reliable and reproducible measurement results when the different transducers are used.

Referring to FIG. 3 with the above criteria in mind, the spectrum (A), which is the "reference spectrum", will lead to the elimination of the transducer corresponding to spectrum (C), selection of the transducer corresponding to the spectrum (B) since the amplitude thereof may be corrected by calibration to correspond to spectrum (A), and also selection of the transducer with spectrum (D) since the form thereof is approximately identical to that of spectrum (A) within an acceptable tolerance of 1 dB, for example. This tolerance, given by way of example, may be varied depending on the required accuracy of measurement.

With the method in accordance with the invention using frequency spectrum analysis, in order to obtain reliable verification results, the selection of the transducers is made by retaining as usable only transducers for which the frequency spectra, obtained under the conditions specified above, are identical at least as to their form.

For the above-described method to be reliable, it is necessary that the measurement chain used for testing the transducers should have the same characteristics as the reference measurement chain. Indeed, each component of the chain has an influence on the form of the spectrum obtained. It is therefore advisable, in the case where at least two inspection or testing apparatuses are used, to define precisely each of the components of the chain, especially the elements achieving the excitation of the transducers, namely the electrical pulse generator, the excitation pulse, and the cable connecting the generator to the transducer.

In one application of the method in accordance with the invention for example, a user of ultrasonic inspection apparatus will define a form of spectrum to which his transducer supplier will have to keep, and the supplier will have to possess an inspection apparatus comprising components which are identical to those of his customer, as mentioned above.

The method in accordance with the invention may also be used during the life of the selected transducers to check their performance. A transducer will be discarded when, as a consequence of ageing, the spectrum obtained under the specified conditions is no longer identical, at least as to its form, to the reference spectrum.

We claim:

1. A method of selecting ultrasonic transducers for use in an ultrasonic inspection apparatus, comprising the steps of:
   determining the frequency spectrum of the echo obtained from a specific reflector using a focusing reference transducer;
   determining the frequency spectrum of the echo obtained from said reflector using a focusing test transducer under the same conditions as said focusing reference transducer, wherein the focusing reference transducer and the focusing test transducer have a common foci at the specific reflector;
   comparing the form of the frequency spectrum obtained using said focusing heat transducer with the form of the frequency spectrum obtained using said focusing reference transducer; and
   selecting said focusing test transducer for use in said ultrasonic inspection apparatus only if the forms of the frequency spectra of the focusing test transducer and the focusing reference transducer are substantially identical.

2. A method according to claim 1, wherein said specific reflector is a plane having dimensions which are greater than the emission diameter of the ultrasonic beams emitted by the transducers.

3. A method according to claim 2, wherein said specific reflector plane is perpendicular to the direction of propagation of the ultrasonic waves emitted by the said transducers.

4. A method according to claim 1, wherein the amplitude of the frequency spectrum of the selected transducer is adjusted by adjusting at least one of amplification and attenuation of the inspection apparatus.

5. A method according to claim 1, wherein the excitation conditions of said transducers are predetermined.

* * * * *